(12) United States Patent
Okoda

(10) Patent No.: US 7,092,491 B2
(45) Date of Patent: Aug. 15, 2006

(54) RADIATION IMAGE TAKING APPARATUS, RADIATION IMAGE TAKING SYSTEM, AND RADIATION IMAGE TAKING METHOD

(75) Inventor: Keiji Okoda, Kanagawa (JP)

(73) Assignee: Canon Kabushiki Kaish, Tokyo (JP)

( * ) Notice: Subject to any disclaimer, the term of this patent is extended or adjusted under 35 U.S.C. 154(b) by 50 days.

(21) Appl. No.: 10/927,976

(22) Filed: Aug. 27, 2004

(65) Prior Publication Data
US 2005/0047549 A1    Mar. 3, 2005

(30) Foreign Application Priority Data
Aug. 29, 2003    (JP) ............................. 2003-209517

(51) Int. Cl.
*H05G 1/28*    (2006.01)
(52) U.S. Cl. ...................... 378/162; 378/205
(58) Field of Classification Search ............... 378/162, 378/163, 164, 205, 98.8; 250/584, 586, 587
See application file for complete search history.

(56) References Cited

U.S. PATENT DOCUMENTS

| | | | |
|---|---|---|---|
| 4,242,587 A | 12/1980 | Lescrenier | 250/252 |
| 5,539,798 A | 7/1996 | Asahina et al. | 378/98.5 |
| 6,354,737 B1 | 3/2002 | Huffe et al. | 378/205 |
| 6,542,579 B1 * | 4/2003 | Takasawa | 378/165 |
| 2001/0033682 A1 | 10/2001 | Robar et al. | 382/132 |
| 2002/0067799 A1 | 6/2002 | Mitchell et al. | 378/62 |
| 2003/0091150 A1 | 5/2003 | Barber et al. | 378/189 |

FOREIGN PATENT DOCUMENTS

| | | |
|---|---|---|
| DE | 10151236 | 5/2003 |
| JP | 2002-291730 | 10/2002 |
| JP | 2002291730 | 10/2002 |

OTHER PUBLICATIONS

English Abstract for Japanese Patent Application Laid-Open No. 2002-291730.
European Patent Office - Patent Abstracts of Japan for Publication No. 2002291730 published Oct. 8, 2002.
Dialog Abstract for Patent Number DE 10151236 published May 8, 2003.
European Patent Office Communication dated Sep. 2, 2005 in corresponding application PCT/04020315.0-2202.

* cited by examiner

*Primary Examiner*—Edward J. Glick
*Assistant Examiner*—Jurie Yun
(74) *Attorney, Agent, or Firm*—Morgan & Finnegan LLP

(57) ABSTRACT

The present invention relates to a radiation image taking apparatus including: a radiation image acquisition portion that acquires an electronic image based on a radiation transmitted through an object and outputs the electronic image; an image taking direction designation portion that designates a posture of the object with respect to the radiation image acquisition portion; a display portion that displays the posture of the object on at least one plane of the radiation image acquisition portion; and a coordinate conversion portion that performs coordinate conversion of the electronic image. The radiation image taking apparatus further includes a control portion that controls the displaying of the posture by the display portion and the coordinate conversion by the coordinate conversion portion based on the posture designated by the image taking direction designation portion.

18 Claims, 15 Drawing Sheets

RADIATION IMAGE TAKING APPARATUS, RADIATION IMAGE TAKING SYSTEM, AND RADIATION IMAGE TAKING METHOD

BACKGROUND OF THE INVENTION

1. Field of the Invention

The present invention relates to a construction of a radiation image taking apparatus that uses a radiation detection means. In particular, the present invention relates to a technique suited for the designation of an image taking direction of an object with respect to a radiation image taking apparatus.

2. Related Background Art

Conventionally, a film/screen method, with which radiation image taking is performed by combining a photosensitive film (X-ray detection means) serving as a two-dimensional detection plane with a phosphor having sensitivity to X rays, has been most commonly used to take an X-ray image. In addition, in recent years, a method called "computed radiography (CR) method" has also been put into practical use. This method is a system where a radiation transmission image is first accumulated as a latent image in an imaging plate serving as a two-dimensional detection plane and then the latent image is read out from the imaging plate by irradiating excitation light onto the imaging plate. Aside from this, with the recent advancement of a semiconductor process technique, an apparatus has also been developed which takes an X-ray image in a like manner using an X-ray detection sensor composed of multiple photoelectric conversion elements as a two-dimensional detection plane. A system of this type has an advantage that it is possible to record an image having an extremely wide radiation exposure range as compared with the conventional radiograph system using a photosensitive film. That is, after X rays in a wide dynamic range are read with the X-ray detection sensor and are converted into an electrical signal, a radiation image is outputted as a visible image to a recording material (such as a photosensitive material) or a display apparatus (such as a CRT) using the electrical signal, thereby making it possible to obtain a radiation image that is hard to be influenced by variations in radiation exposure amount.

FIG. 22 is a schematic diagram showing a radiation image taking system that uses the semiconductor sensor described above. In an X-ray image taking apparatus 2201, an X-ray detection sensor 2202 is embedded which has a detection plane where multiple photoelectric conversion elements are arranged in a two-dimensional manner. With this construction, X rays emitted from an X-ray generation portion 2203 are irradiated onto an object 2206 and X rays transmitted through the object 2206 are detected by the X-ray detection sensor 2202. An image signal outputted from the X-ray detection sensor 2202 is subjected to digital image processing in an image processing means 2204 and is displayed on a monitor 2205 as an X-ray image of the object 2206. Such an X-ray detection sensor is called "planar detector", "flat panel", or the like due to its shape.

When image taking is performed with the various systems described above, in order to position the object in a detection area of the detection means, it is required to indicate the detection area of the detection means and the like on the enclosure of the planar detector. A method for displaying the detection area of the detection means on the enclosure of the planar detector is proposed in Japanese Patent Application Laid-Open No. 2002-291730.

FIG. 23 shows an example of a conventional transportable planar detector. In this drawing, reference numeral 2301 denotes a transportable X-ray image taking apparatus in which an X-ray detection sensor (not shown) is embedded which has a detection plane where multiple photoelectric conversion elements are arranged in a two-dimensional manner. Reference numeral 2302 indicates a cover for an enclosure plane of the X-ray image taking apparatus 2301 in a portion where X rays are irradiated, with the cover being made of a material having a high X-ray transmittance and being a carbon plate or the like. Reference numeral 2303 represents a rectangular frame line representing the detection plane of the X-ray detection sensor (not shown). Reference numeral 2304 denotes a center line in a short-side direction of the rectangular detection plane and reference numeral 2305 indicates a center line in a long-side direction thereof. Reference numeral 2307 represents a cable connecting the X-ray image taking apparatus 2301 to a control apparatus (not shown), with electrical signals that are control signals and an electronic image being communicated between the X-ray image taking apparatus 2301 and the control apparatus through the cable. Reference numeral 2308 denotes an object, with a case where the object 2308 is a right hand of a person being illustrated in the drawing as an example. In FIG. 23, the upper left corner of the frame line 2303 is set as the image coordinate original point of the X-ray detector (not shown). Also, in the drawing, the downward direction is set as the positive direction of an X axis and the rightward direction is set as the positive direction of a Y axis.

FIG. 24 is an explanatory diagram of a case where an image taken with the X-ray image taking apparatus 2301 is displayed on a monitor 2401. In this drawing, reference numeral 2403 denotes an object and reference numeral 2402 indicates an image area. In this illustrated case, a definition has been formulated in advance so that an image coordinate original point is positioned at the lower left corner of the display apparatus.

FIG. 25 shows a case where the same X-ray image taking apparatus 2301 as in FIG. 23 is set under a state where it has been rotated by 180°. The same reference numerals as in FIG. 23 denote the same members. In this drawing, the image original point is changed to the lower right corner, although the cover 2302, the frame line 2303, and the center line 2304 have symmetric shapes and therefore are not changed from their states shown in FIG. 23. Consequently, if image taking is performed by determining the detection plane for the object 2308 in the same direction as in FIG. 23 without giving consideration to the fact that the X-ray image taking apparatus 2301 has been rotated by 180°, image displaying on the monitor 2401 is performed in the manner shown in FIG. 26 where an object 2601 is displayed under a state where it has been rotated by 180° from the state of the object 2403 shown in FIG. 24. That is, in this case, the object is not displayed in an original observation direction.

As described above, when image taking is performed using a transportable X-ray image taking apparatus or an X-ray image taking apparatus embedded in a bed, various relative positional relationships between the two-dimensional detection plane and the object are possible, which leads to a problem in that it is not guaranteed that a taken image is displayed in a desired direction at the time of image displaying. Also, there is a case where printing is performed by inserting an object name, an image taking date and time, and the like (hereinafter referred to as the "annotation") in the upper portion or the like of an electronic image. In this case, there occurs a problem in that the positional relationship between the annotation and the object does not become a desired relationship at the time of displaying.

In the conventional example described above, even in the case shown in FIG. 26 where the image is displayed in a direction that is different from the original direction, it is possible to obtain the same positional relationship as in FIG. 24 by rotating the image, although this results in a situation where the convenience of the system, whose advantage lies in the immediacy of image displaying is lost. It is possible for an operator to define in advance the correspondence between the coordinate original point and the coordinate system of a taken image and a display portion of the display apparatus at the time of displaying, although it is usual that this correspondence is defined in units of parts to be image-taken. Therefore, when the same part is image-taken in different directions like in this example, there occurs a problem in that it is impossible to perform displaying in a desired direction without delay.

SUMMARY OF THE INVENTION

The present invention has been made in view of the problems described above, and is aimed at making it possible to designate the image taking direction of an object with respect to an X-ray image taking apparatus.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 1:
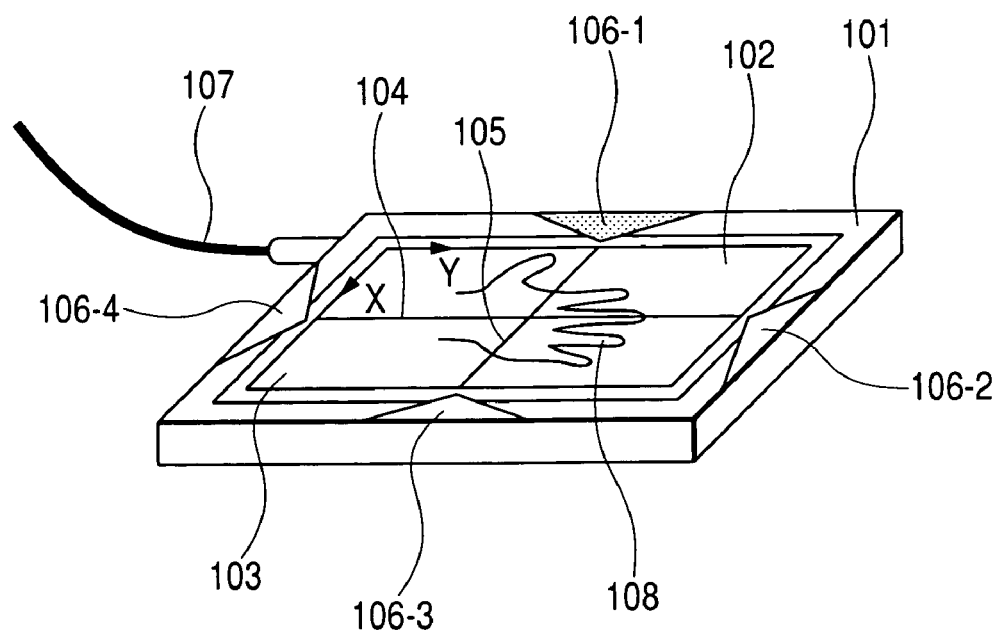
FIG. 1 is a perspective view illustrating a schematic construction of an X-ray image taking apparatus of a first embodiment of the present invention.

Preferred embodiments of the present invention will now be described in detail in accordance with the accompanying drawings.

The present invention will now be described in detail below based on embodiments illustrated in FIGS. 1 to 21. In particular, in each following preferred embodiment, a case where X rays among radiation are used will be described.

FIGS. 1 to 6 each illustrate a first embodiment of the present invention. In these drawings, the same reference numerals denote the same members.

First, a construction of this embodiment will be described with reference to FIG. 1. In this drawing, reference numeral 101 denotes a transportable X-ray image taking apparatus in which a X-ray detection sensor (not shown) is embedded which has a detection plane where multiple photoelectric conversion elements are arranged in a two-dimensional manner. Reference numeral 102 indicates a cover for an enclosure plane of the X-ray image taking apparatus, with this cover being made of a material having a high X-ray transmittance and being a carbon plate or the like. Reference numeral 103 represents a rectangular frame line expressing the detection area of the X-ray detection sensor (not shown). Reference numeral 104 denotes a center line in a short-side direction of the rectangular detection area. Reference numeral 105 indicates a center line in a long-side direction thereof.

Reference numerals 106-1 to 106-4 represent indicators that indicate the direction of the detection plane and are constructed so that they are capable of being electrically turned on/off. Also, the indicators 106-1 to 106-4 are constructed so that they perform light emission in two or more colors. To do so, for instance, these indicators each include red and blue lamps. With this construction, the indicators constitute a display portion. In this drawing, each indicator 106 is positioned outside the frame line 103 and in the vicinity of the center of one of long and short sides of the frame line 103. Reference numeral 107 denotes a cable connecting the X-ray image taking apparatus 101 to a control apparatus (not shown), with control signals and an electronic image being communicated between the X-ray image taking apparatus 101 and the control apparatus through the cable 107. Reference numeral 108 indicates an object, with a case where the object 108 is the right hand of a person being illustrated in the drawing as an example. In the illustrated example, an operator performs image taking by always directing the thumb side of the right hand toward the indicator 106-1 that performs light emission all the time. In FIG. 1, the upper left corner of the frame line 103 is set as the coordinate original point of the two-dimensional detection plane (not shown). Also, in FIG. 1, when the indicator 106-1 performs light emission in red, the downward direction of the frame line 103 becomes the positive direction of an X axis and the rightward direction thereof becomes the positive direction of a Y axis.

In contrast to this, when the indicator 106-1 performs light emission in blue, the long-side side indicates the positive direction of the X axis and the short-side side indicates the positive direction of the Y axis. That is, it is possible for the image taking person to recognize the coordinate original point and the coordinate system of the detection plane with reference to the light emission by the indicators. With this construction, the image taking person becomes capable of recognizing a direction in which he/she should arrange the object with respect to the X-ray image taking apparatus 101. Hereinafter, the combination of light emission, non-light emission, and light emission color of each indicator will be referred to as the "pattern". Also, when the gravity center position of the detection plane is set as a rotation center, the pattern is set so as to be a pattern that is not rotation-symmetric. With this construction, it becomes possible to uniquely determine the coordinate original point. Here, it is assumed that the relationship among the pattern, the coordinate original point, and the coordinate system was taught to the image taking person in advance.

Figure 2:
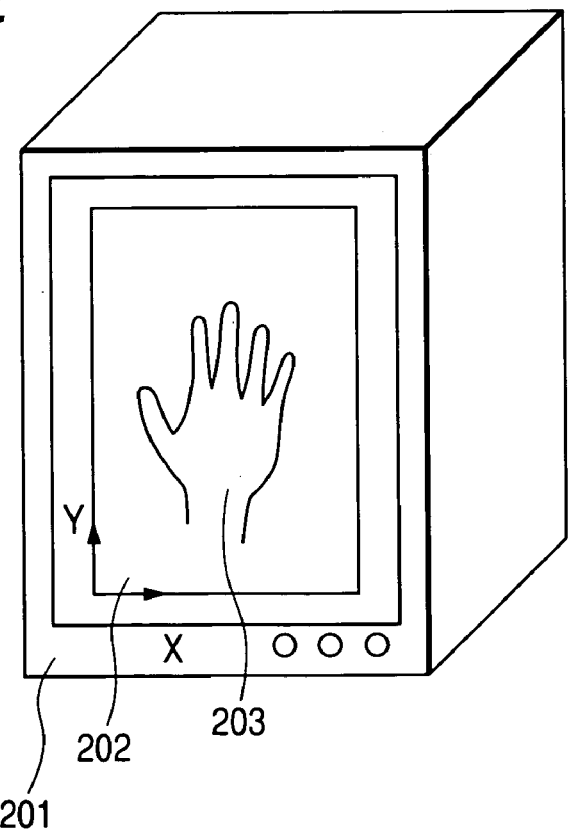
FIG. 2 is a perspective view illustrating an example of displaying on a monitor of the first embodiment.

FIG. 2 is an explanatory diagram where an electronic image taken with the X-ray image taking apparatus 101 is displayed on a monitor 201 (second display portion). In this drawing, reference numeral 203 denotes an object and reference numeral 202 indicates an image area. In this illustrated case, a definition has been formulated in advance so that the coordinate original point of the electronic image is positioned at the lower left corner of the display apparatus, with the positive direction of an X axis being set on the short-side side and the positive direction of a Y axis being set on the long-side side.

Figure 3:
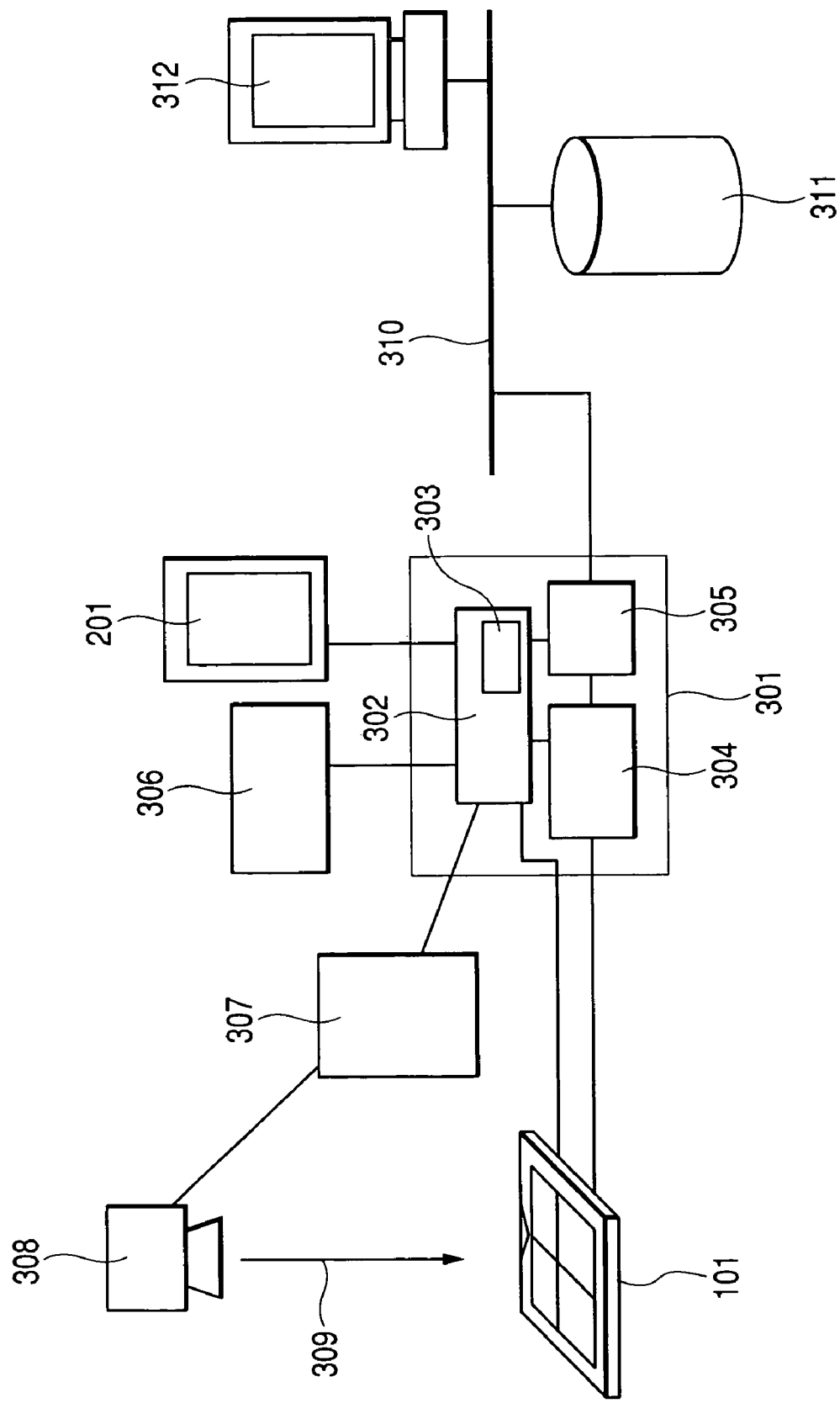
FIG. 3 is a block diagram illustrating a schematic construction of a radiation image taking system using the X-ray image taking apparatus of the first embodiment.

FIG. 3 is a schematic construction diagram of a radiation image taking system including the X-ray image taking apparatus 101 shown in FIG. 1 and the monitor 201 shown in FIG. 2. In FIG. 3, reference numeral 301 denotes a control portion connected to the X-ray image taking apparatus 101, with the control portion 301 including a control means 302, an image processing means 304, a communication means 305, and the like. Also, the control means 302 includes a storage means 303 for storing various settings. Reference numeral 306 indicates an operation portion (image taking direction designation portion) that performs various inputs into the control portion and also instructs displaying of information concerning operations. As information concerning the object, a part name, an image taking posture, and the like are inputted by the operation portion 306, for instance. The control means 302 performs exchange of various control signals with the X-ray image taking apparatus 101. Reference numeral 307 represents an X-ray generation apparatus connected to the control portion 301 and reference numeral 308 indicates an X-ray tube 308 connected to the X-ray generation apparatus 307. With this construction, the X-ray generation apparatus 307 and the control portion 301 mutually inform of their states and exchange synchronization signals at the time of image taking. An electronic image acquired with the X-ray image taking apparatus 101 is transmitted to the image processing portion 304 which then performs desired processing on the electronic image. The electronic image subjected to the processing is sent to a network 310 in a hospital through the communication means 305. Connected to the network 310 are an image database 311 and a workstation for image interpretation 312. Here, it is assumed that the image processing portion 304 includes an A/D converter that A/D-converts an electrical signal from the X-ray detection sensor (X-ray detection means). Note that it is also possible to use a construction where the A/D converter is provided for the X-ray detection sensor (X-ray detection means). In this case, the image processing portion 304 becomes a portion that has only an image processing function for performing gradation conversion processing and the like.

Figure 4:
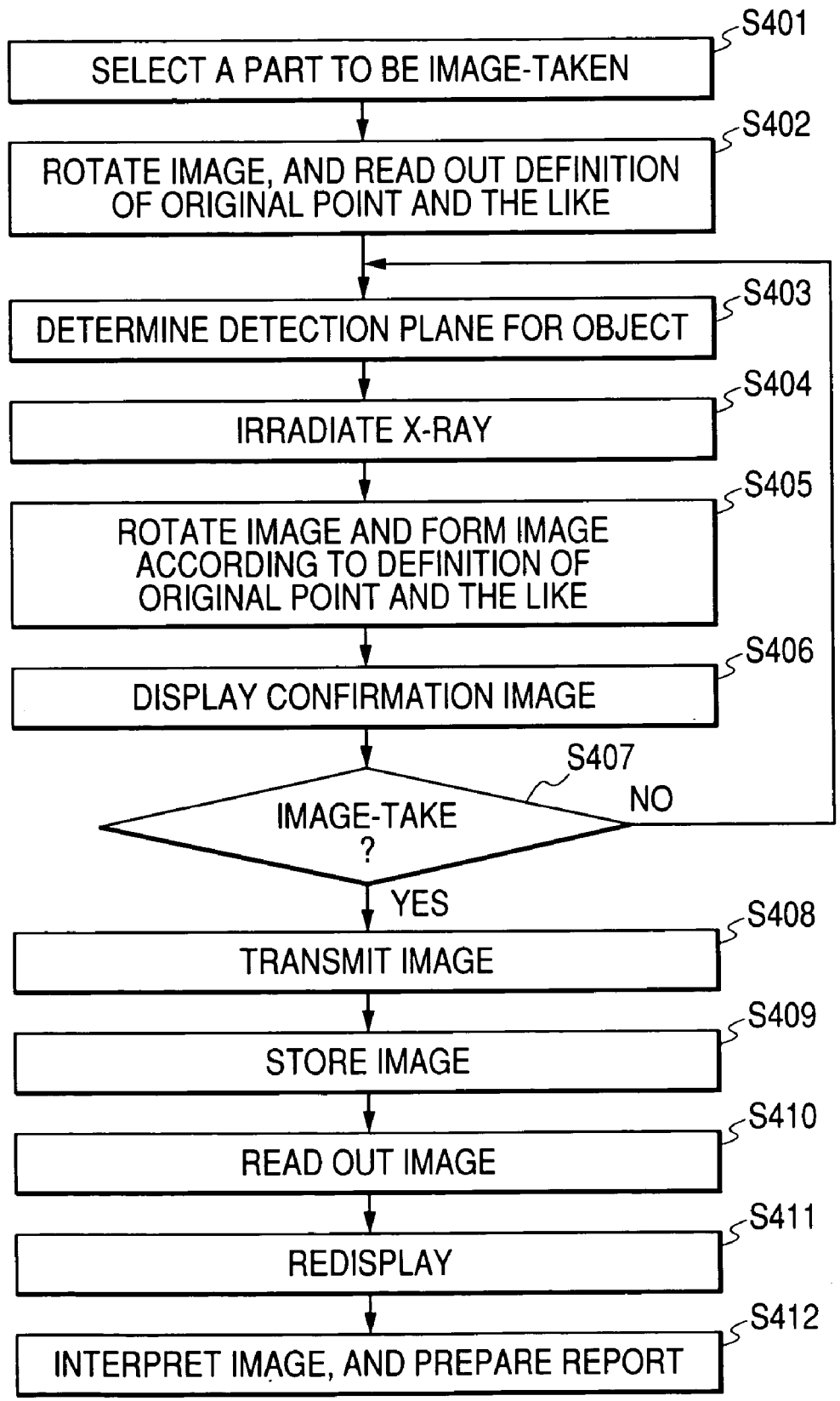
FIG. 4 is a flowchart showing an operation procedure of the first embodiment.

Next, a procedure for taking a radiation image using the X-ray image taking apparatus 101 will be described with reference to a flowchart shown in FIG. 4 and the schematic construction diagram of the image taking system shown in FIG. 3. First of all, a part to be image-taken is selected using the operation portion 306 (S401). Concurrently with this part selection, information defined for the part in advance and concerning a coordinate original point, a coordinate system, image taking conditions, image processing conditions, and the like is read out from the storage means 303 and is recognized by the control means 302 (S402). Here, a setting has been made so that the coordinate original point and the coordinate system of a taken electronic image coincide with the coordinate original point and the coordinate system of the monitor 201. It is possible for the operator to make this setting in advance at desired values through input from the operation portion 306 and to store the values in the storage means 303. Next, the operator determines the detection plane of the X-ray image taking apparatus 101 for the object (S403). When doing so, the object is positioned with reference to the indicators 106 so that the object is set in the same direction at all times. Next, X rays are irradiated from the X-ray tube 308, thereby performing image taking (S404). After this image taking, an electronic image is transmitted to the image processing portion 304 which then subjects the electronic image to desired processing including image rotation and the like (S405). In this example, the image processing portion 304 also has the function of a coordinate conversion portion for converting the coordinates of the image. After that, a confirmation image is displayed on the monitor 201 (S406). When doing so, the aforementioned image rotation setting made for the part coincides with the direction of the object uniquely positioned with reference to the indicators 106, so that the electronic image is displayed in a desired direction at all times. Therefore, an operation for rotating post-displaying image becomes unnecessary, which makes it possible to perform swift work. Then, it is judged whether the image taking has been ended in success using the displayed image. If it is judged that the image taking has ended in failure, image retaking is performed. On the other hand, if it is judged that the image taking has ended in success, a transmission command is inputted from the operation portion 306 (S407). In response to this command, the electronic image is transmitted from the communication means 305 to the electronic image database 311 through the network 310 (S408) and is stored in the electronic image database 311 (S409). The stored electronic image is read out from the electronic image database 311 at the time of image interpretation or the like (S410) and is displayed on a high-resolution monitor of the workstation for image interpretation 312 (S411). An image interpretation doctor interprets the displayed image and prepares a diagnosis report (S412). In the electronic image database 311, the electronic image is stored under a state where it is given an image rotation parameter, so that it becomes possible for the image interpretation doctor to display the electronic image in a desired direction at the time of the displaying on the monitor.

Figure 5:
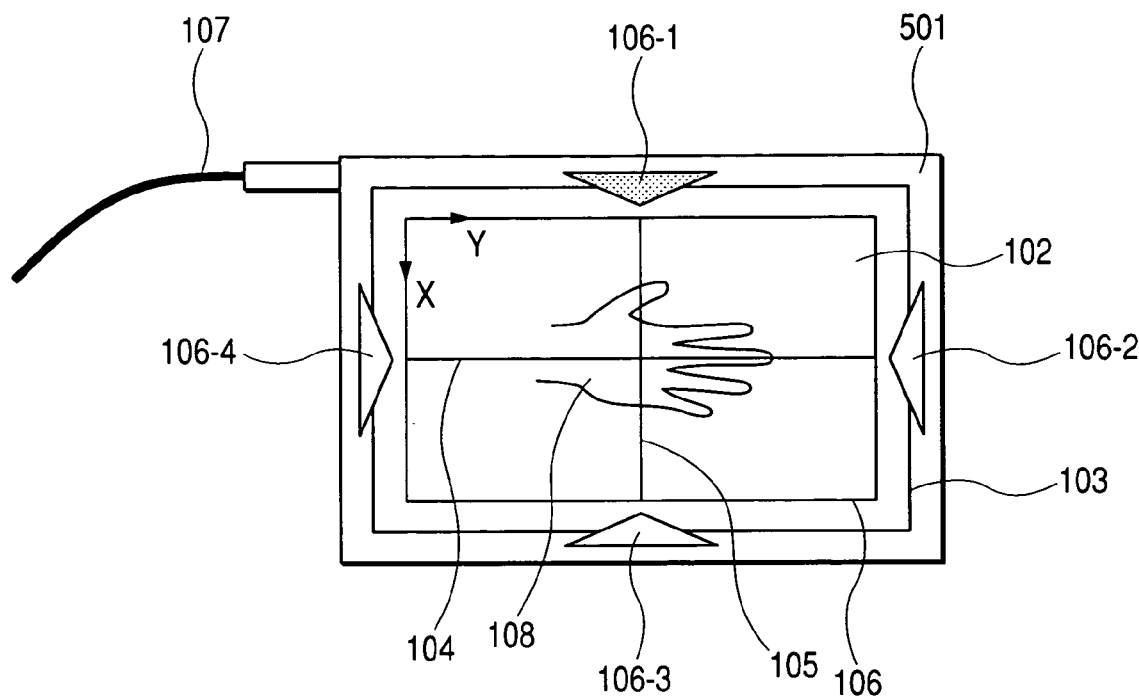
FIG. 5 is a plan view illustrating the schematic construction of the X-ray image taking apparatus of the first embodiment.
Figure 6:
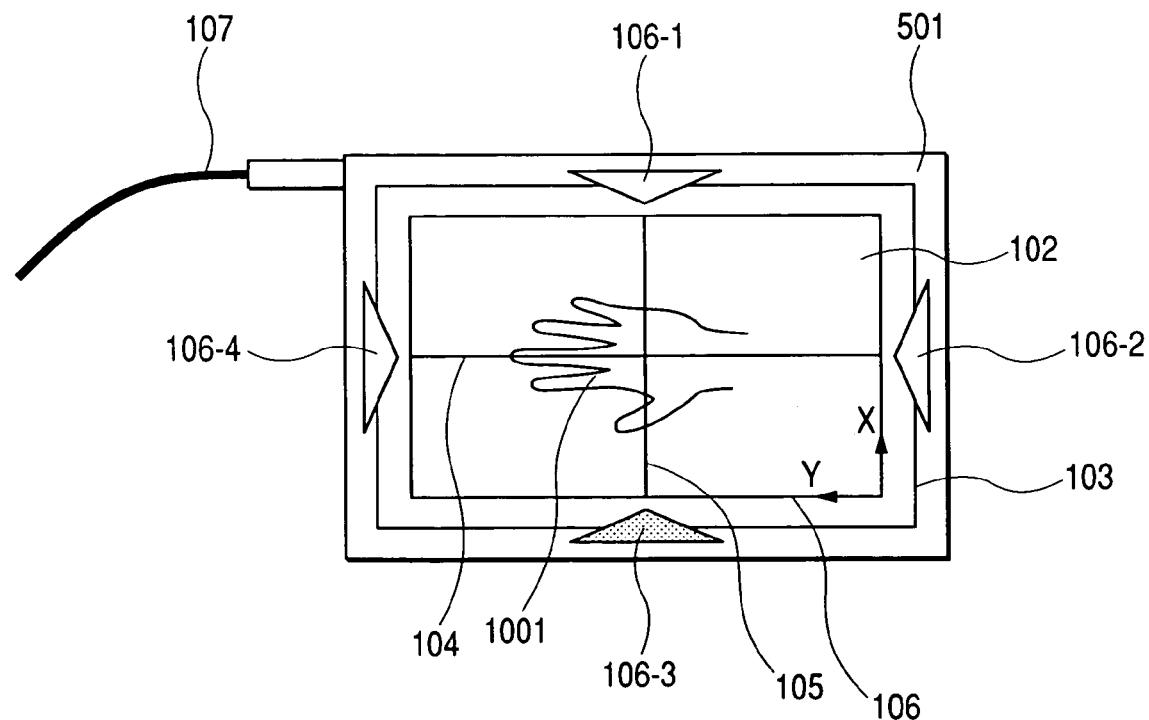
FIG. 6 is another plan view illustrating the schematic construction of the X-ray image taking apparatus of the first embodiment.

FIGS. 5 and 6 are plan views where the object 108 is set with respect to the same X-ray image taking apparatus 101 as in FIG. 1 in different directions. In FIG. 5, the image original point is set at the upper left corner of the frame line 103. On the other hand, in FIG. 6, the image original point is set at the lower left corner of the frame line 103. That is, in these drawings, a coordinate system in the case where a certain indicator performs light emission in red is illustrated. With this construction, in each of the cases shown in FIGS. 5 and 6, it becomes possible for the operator to recognize the coordinate original point and the coordinate system of the detection plane with ease and to correctly position the object 108 by directing the thumb side of the hand toward the indicator 106 emitting light in red like in the case shown in FIG. 1. Therefore, even when image taking is performed under the state shown in FIG. 6, it is possible to display the object in a desired direction as shown in FIG. 2.

It is possible to almost uniquely determine whether the object 108 should be image-taken in the direction shown in FIG. 5 or in another direction (such as the direction shown in FIG. 6) in a certain image taking system, although the determined image taking direction does not necessarily become an appropriate image taking direction in another apparatus or another facility. That is, it is possible to conceive various appropriate image taking directions depending on the arrangement of apparatuses, the shape of an image taking room, the moving paths of a subject and an operator, the preference and experience of the operator, and the like. Here, it is assumed that when the cable 107 is positioned in the direction shown in FIGS. 5 and 6, this cable 107 is positioned appropriately with respect to the arrangement of the X-ray image taking apparatus 101 and the control portion 301 shown in FIG. 3. In this case, if an entrance, through which the subject enters into the image taking room, exists on the left side in the drawings, it is possible for the subject to move in a natural manner in the case shown in FIG. 5. On the other hand, if the entrance exists on the right side in the drawings, it is possible for the subject to move in a natural manner in the case shown in FIG. 6. Accordingly, an effect is also produced that by changing the coordinate original point and the coordinate system as appropriate, it is possible to perform the image taking with more ease.

In addition, an effect is provided that even when printing is performed by making an annotation in the upper portion or the like of an electronic image, it is possible to maintain a desired positional relationship between the object and the annotation.

Next, a second embodiment of the present invention will be described. Here, the same reference numerals as in FIG. 1 denote the same members.

Figure 7:
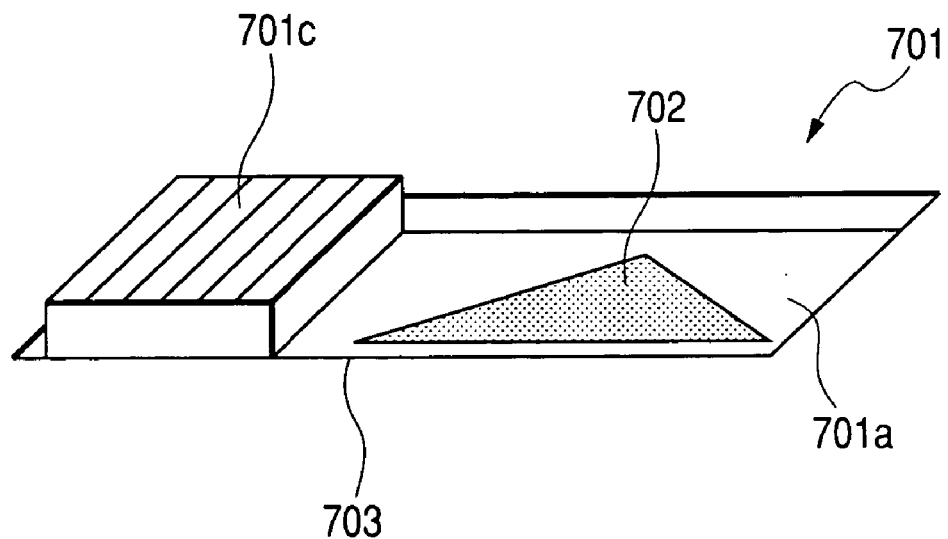
FIG. 7 is an enlarged view of an indicator portion of an X-ray image taking apparatus of a second embodiment.
Figure 8:
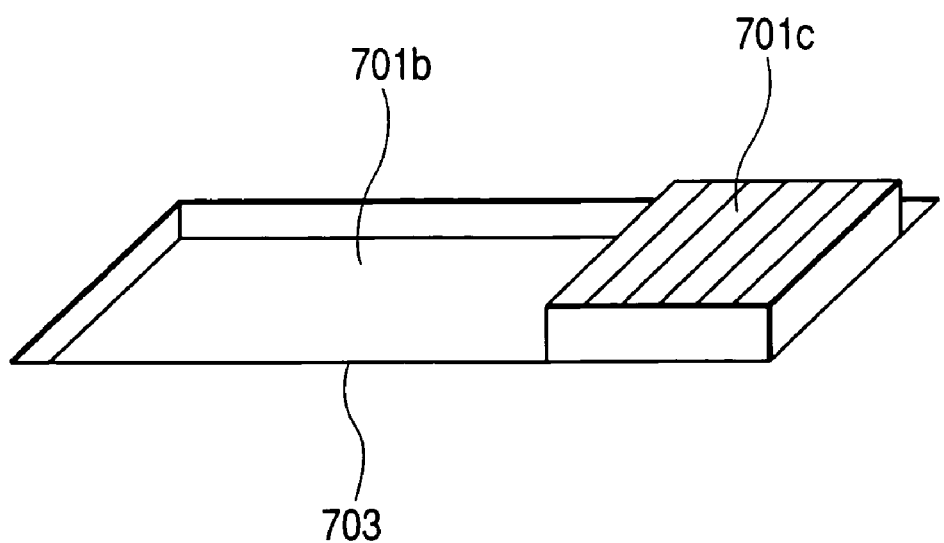
FIG. 8 is another enlarged view of the indicator portion of the X-ray image taking apparatus of the second embodiment.

FIGS. 7 and 8 are each an enlarged view of an indicator portion of the second embodiment of the present invention. Each not-illustrated portion other than the indicator portion is the same as that in the first embodiment. That is, only the indicator portion 106 in the first embodiment is modified in this second embodiment. In FIGS. 7 and 8, reference numeral 701 denotes a sliding indicator portion that has a mechanism with which the indicator portion is capable of moving in a right-left direction in the drawings with respect to an opening portion 703 of an enclosure plane. When a protrusion 701c of the indicator portion 701 exists at a position shown in FIG. 7, a surface 701a, on which an indicator 702 is illustrated, is exposed to the outside through the opening portion 703. On the other hand, when the protrusion 701c is pushed and is moved in the rightward direction from the position shown in FIG. 7, a state shown in FIG. 8 is obtained in which a surface 701b, on which no indicator is illustrated, is exposed to the outside through the opening portion 703. The sliding portion 701 has a mechanism with which it is fixable at the positions shown in FIGS. 7 and 8. Then, when the protrusion 701c is pushed in the horizontal direction with a certain force, the sliding portion 701 set at one of the positions shown in FIGS. 7 and 8 is moved and is set at the other of the positions. By providing such indicator portions at multiple locations of the enclosure plane, it becomes possible for the operator to arrange the indicators at desired positions. Also, it is possible for the operator to change the display positions of the indicators with ease. These sliding indicator portions are driven by a motor (not shown) and the motor receives control by the control portion 302. It is also possible to express a coordinate system by providing two kinds of indicators 702 that are in red and blue along one long side.

It should be noted here that in the above description, the sliding portion 701 is motor-driven, although it is also possible to use a construction where the sliding portion 701 is slid manually. In this case, the control by the control portion 302 becomes unnecessary.

Figure 9:
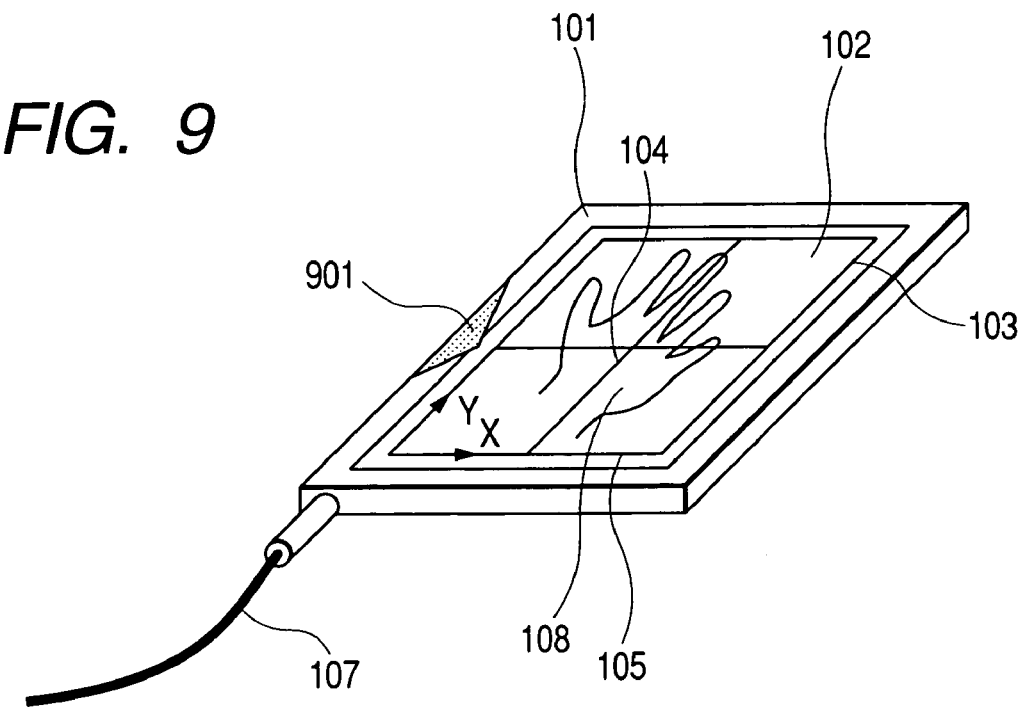
FIG. 9 is a perspective view illustrating a schematic construction of an X-ray image taking apparatus of a third embodiment.
Figure 10:
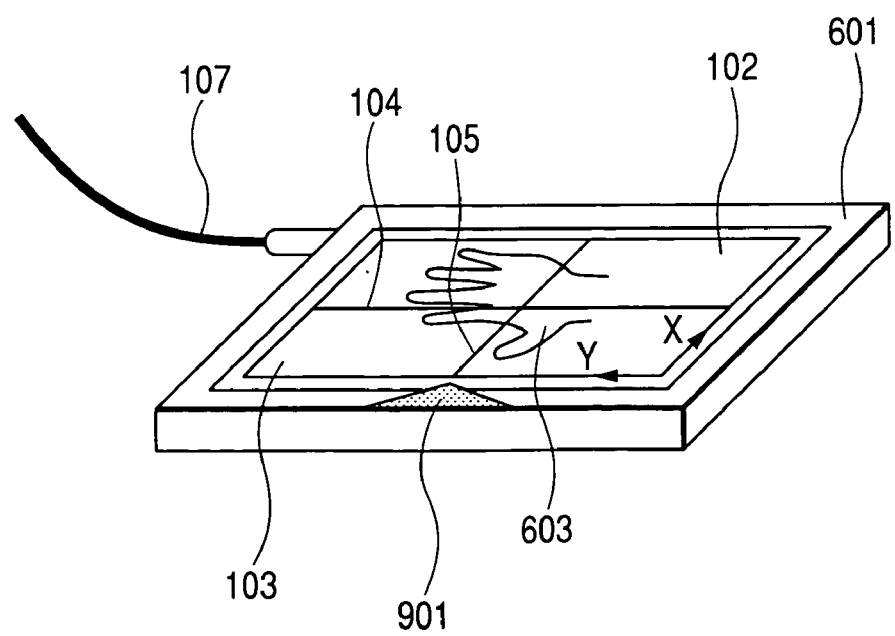
FIG. 10 is another perspective view illustrating the schematic construction of the X-ray image taking apparatus of the third embodiment.

FIGS. 9 and 10 each show a third embodiment of the present invention that differs from the first embodiment in that the indicators 106 shown in FIG. 1 are changed to an indicator 901 that is movable to an arbitrary position and is fixable at the position after the movement.

Various forms are conceivable as a mechanism for moving and fixing the indicator. In the case shown in FIGS. 9 and 10, the triangular indicator 901 is produced as a sticker having an adhesive on its undersurface. With this construction, it becomes possible for the operator to stick the indicator 901 at his/her preferred position. In this case, the control by the control portion 302 becomes unnecessary.

Figure 11:
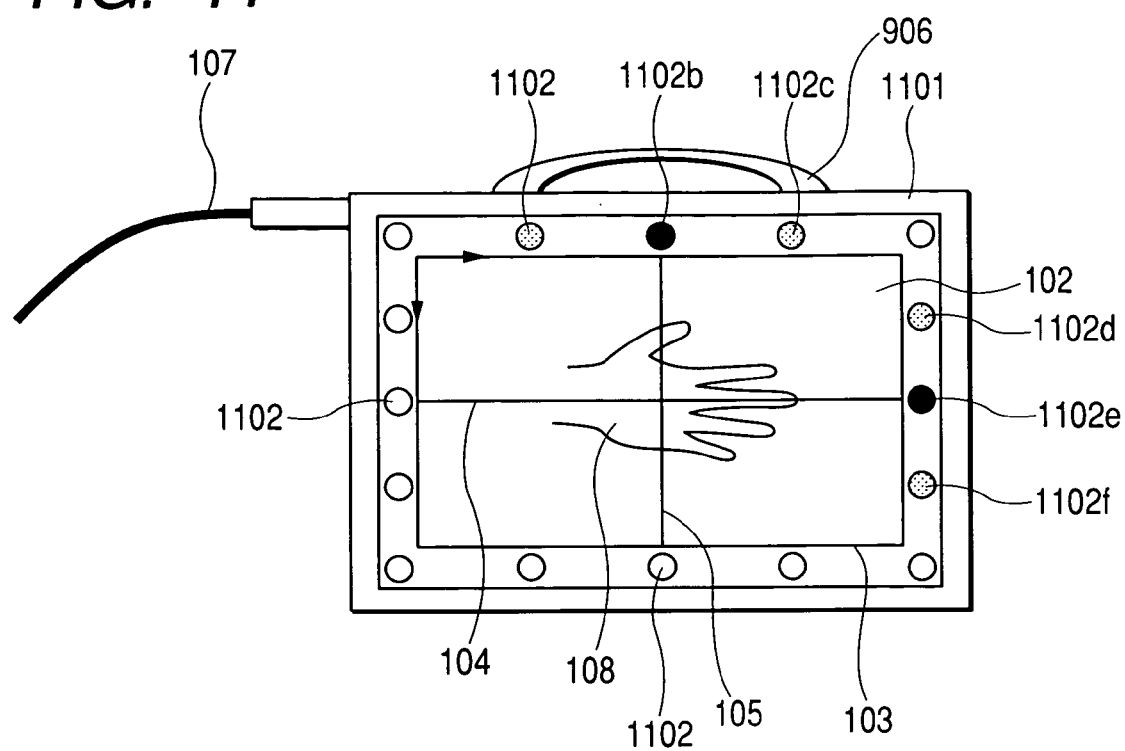
FIG. 11 is a plan view illustrating a schematic construction of an X-ray image taking apparatus of a fourth embodiment.

FIG. 11 is a plan view showing a fourth embodiment of the present invention. In this embodiment, 16 indicators 1102 that are each capable of being electrically turned on/off are arranged for an X-ray image taking apparatus 1101. Here, each indicator 1102 is controlled by a control portion (not shown) and is set under one of three states: a state where it is turned on to emit light in red (indicators 1102b and 1102e in FIG. 11); a state where it is turned on to emit light in green (indicators 1102a, 1102c, 1102d, and 1102f in FIG. 11); and a state where it is turned off (all of the remaining indicators 1102 in FIG. 11). Each indicator turned on in red indicates the direction of the object and also represents the center lines of the object. On the other hand, each indicator turned on in green indicates the approximate range of the object and it is possible for an operator to adjust the irradiation range of X rays with reference to this range. With this construction, in addition to the same effect as in the first embodiment, an effect is provided that it is possible to provide the operator with more detailed information.

Figure 12:
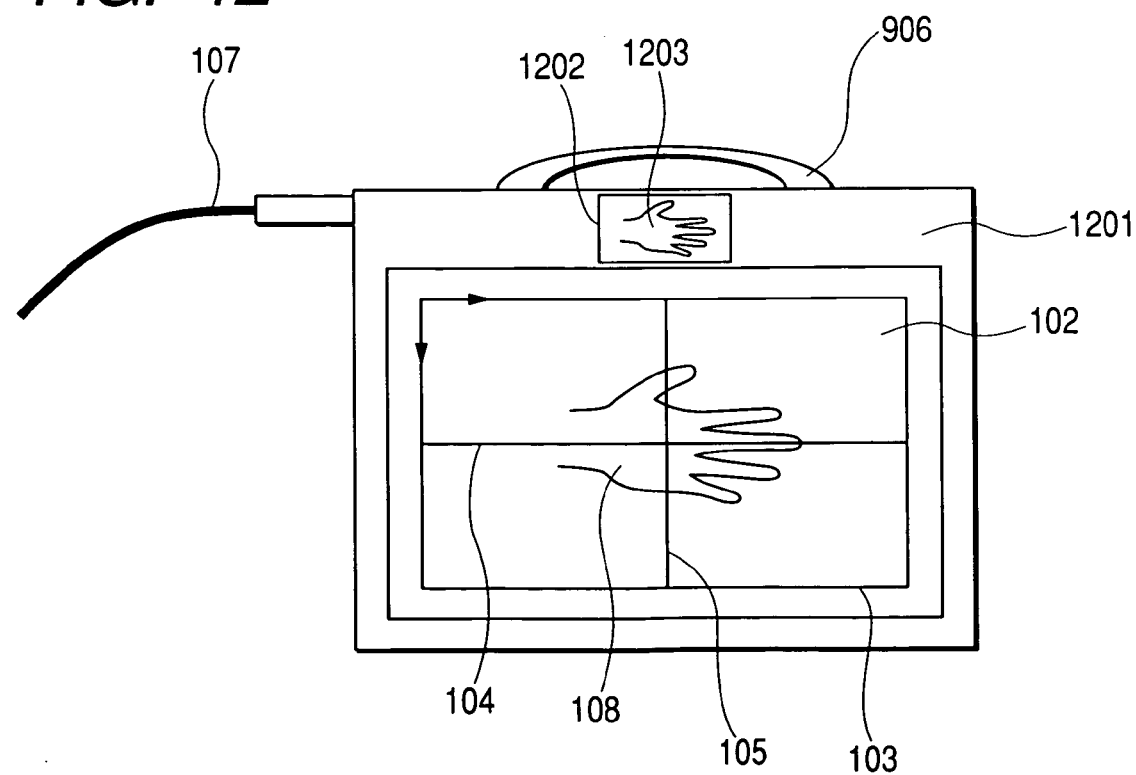
FIG. 12 is a plan view illustrating a schematic construction of an X-ray image taking apparatus of a fifth embodiment.

FIG. 12 is a plan view showing a fifth embodiment of the present invention. In this embodiment, a display portion 1202 (second display means), such as a liquid crystal display apparatus, that displays a two-dimensional image is provided for an X-ray image taking apparatus 1201. The display portion 1202 is capable of displaying a two-dimensional image expressing the schematic shape or the like of an object. When a part to be image-taken is selected, a schematic shape 1203 of the part is displayed on the display portion 1202 (second display means). The direction of the schematic shape 1203 coincides with a direction that is appropriate at the time of displaying after image taking. With this construction, an operation for storing the positional relationship between an indicator and an object (such as the alignment of a right hand thumb with an indicator) becomes unnecessary, which makes it possible to position the object more intuitively. As a result, work efficiency is further improved.

Next, an example where the display position of the indicator in the third embodiment is changed will be described. The same reference numerals as in FIG. 1 denote the same members.

Figure 13:
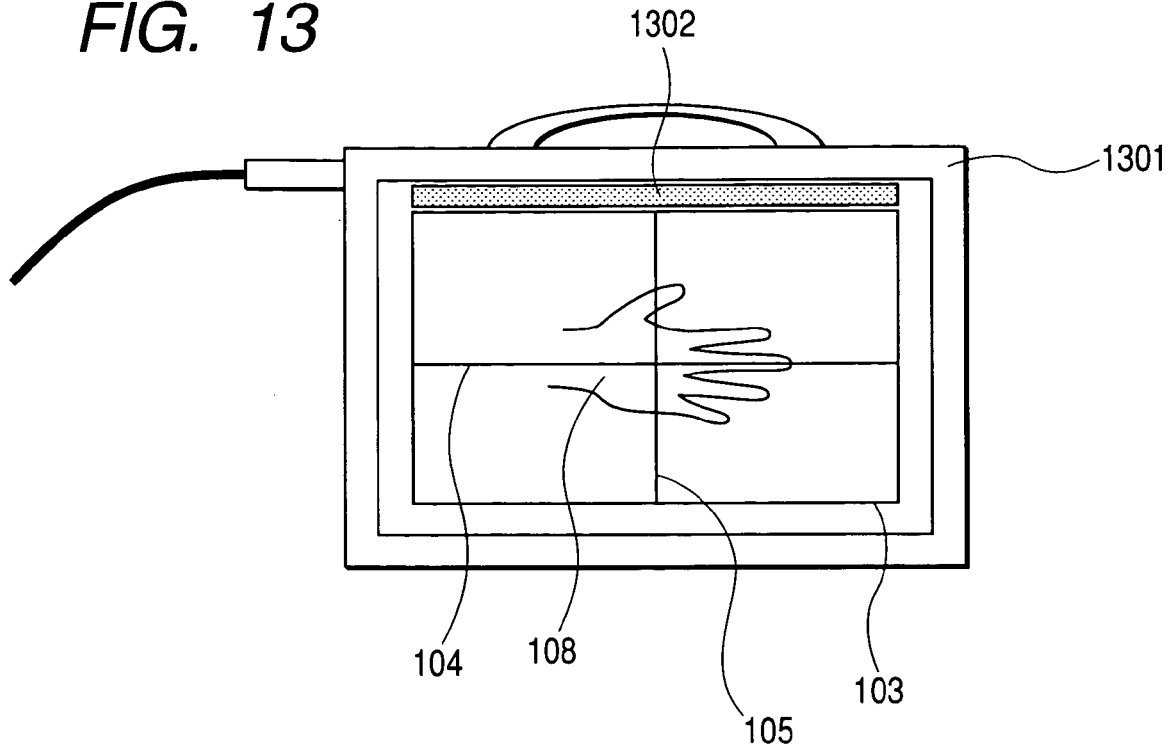
FIG. 13 is a plan view illustrating a schematic construction of an X-ray image taking apparatus of a sixth embodiment.

FIG. 13 shows a sixth embodiment where an indicator 1302 is arranged along one of the long sides of a frame line 103 of an enclosure plane of an X-ray image taking apparatus 1301. The indicator 1302 has a length that is approximately equal to the total length of the long side of the frame line 103.

Figure 14:
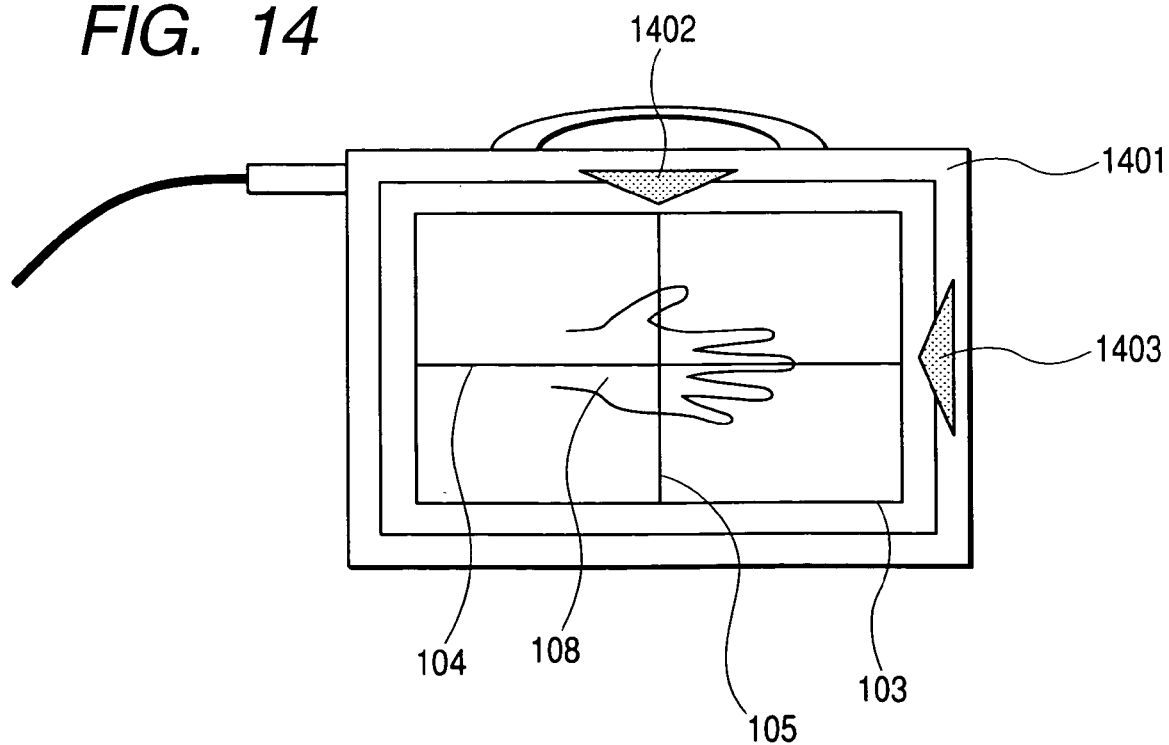
FIG. 14 is a plan view illustrating a schematic construction of an X-ray image taking apparatus of a seventh embodiment.

FIG. 14 shows a seventh embodiment where like in the third embodiment, an indicator 1402 is arranged outside a frame line 103 of an enclosure plane of an X-ray image taking apparatus 1401 and in the vicinity of the center of one of the long sides of the frame line 103. In this seventh embodiment, however, an indicator 1403 is also provided outside the frame line 103 and in the vicinity of the center of one of the short sides of the frame line 103.

Figure 15:
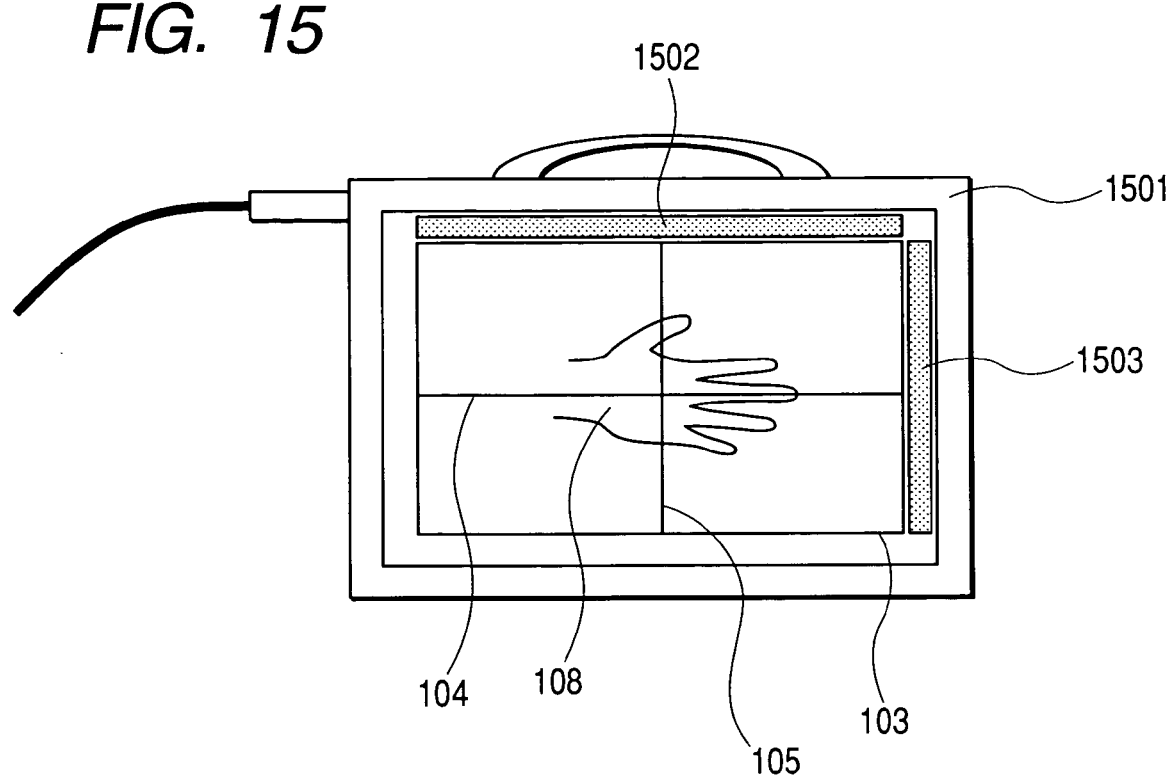
FIG. 15 is a plan view illustrating a schematic construction of an X-ray image taking apparatus of an eighth embodiment.

FIG. 15 shows an eighth embodiment where like in the sixth embodiment, an indicator 1502 is arranged along one of the long sides of a frame line 103 of an enclosure plane of an X-ray image taking apparatus 1501. In this eighth embodiment, however, an indicator 1503 is also arranged along one of the short sides of the frame line 103.

Figure 16:
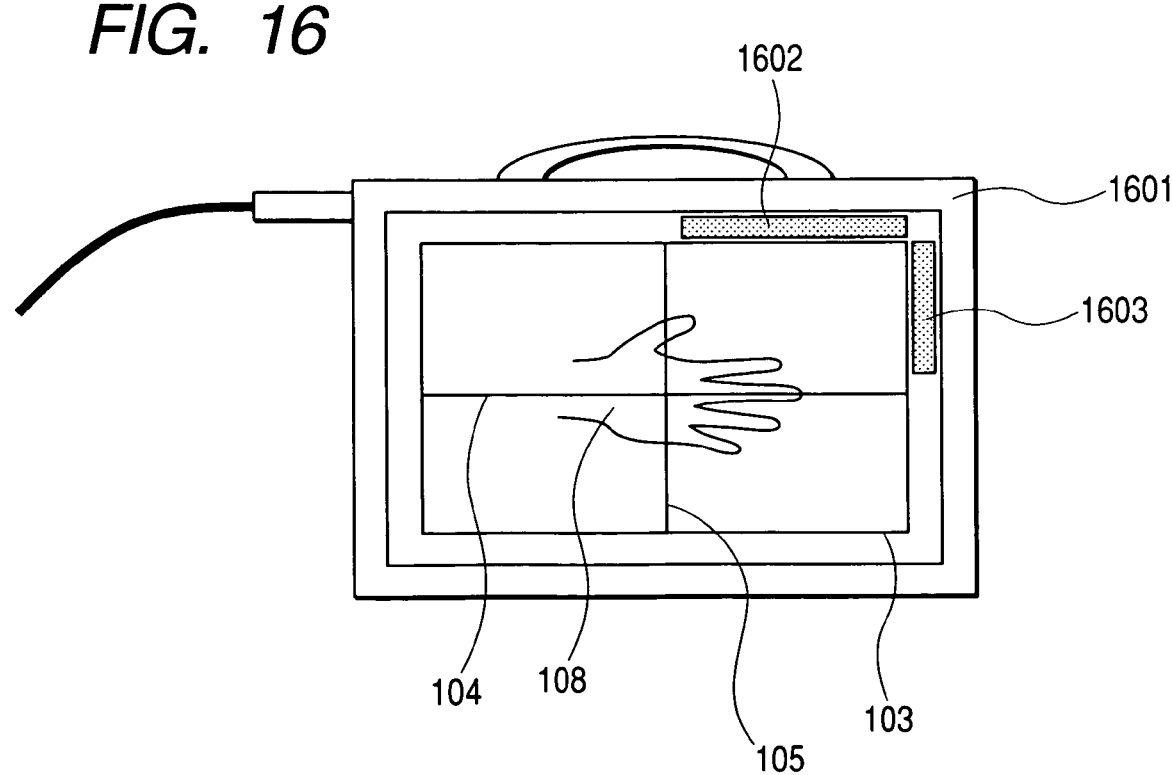
FIG. 16 is a plan view illustrating a schematic construction of an X-ray image taking apparatus of a ninth embodiment.

FIG. 16 shows a ninth embodiment where indicators 1602 and 1603 are arranged outside a frame line 103 of an enclosure plane of an X-ray image taking apparatus 1601, with the indicator 1602 having a length that is around ½ of the length of the long sides of the frame line 103 and the indicator 1603 having a length that is around ½ of the length of the short sides of the frame line 103. The indicator 1602 is arranged outside the frame line 103 and between the center of one of the long sides of the frame line and a certain corner and the indicator 1603 is arranged outside the frame line 103 and between the center of one of the short sides of the frame line and the certain corner.

Figure 17:
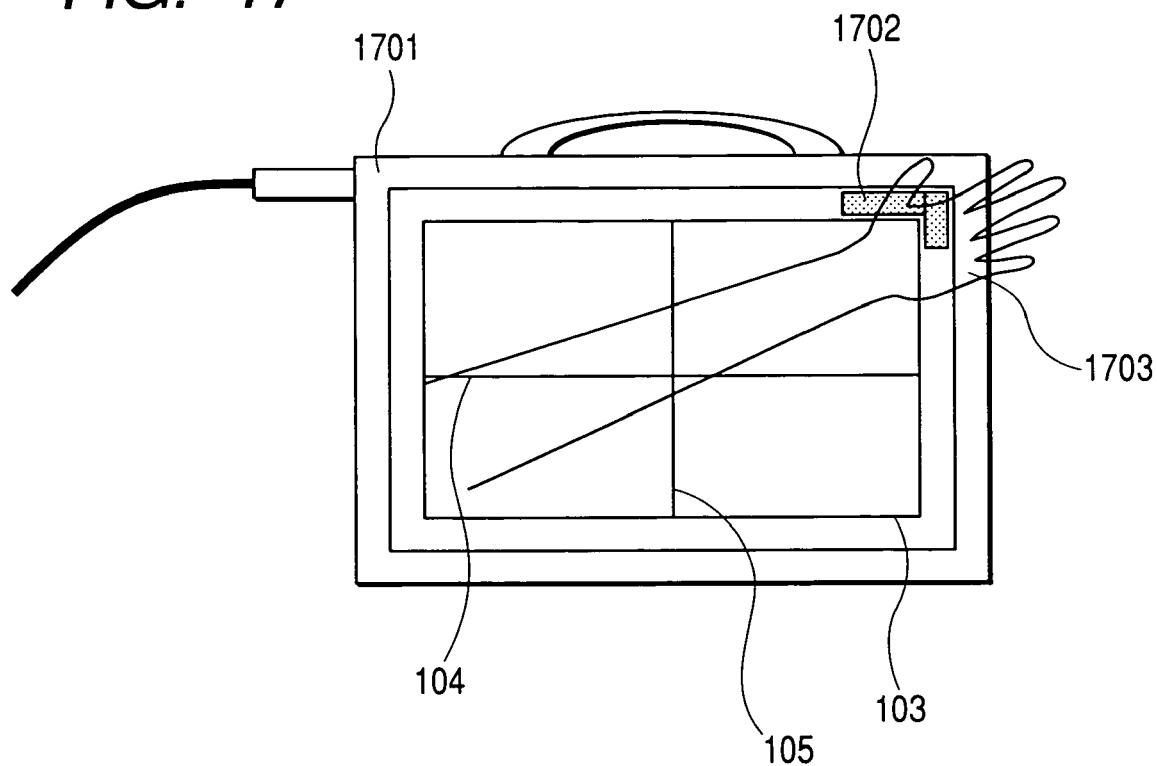
FIG. 17 is a plan view illustrating a schematic construction of an X-ray image taking apparatus of a tenth embodiment.

FIG. 17 shows a tenth embodiment where an indicator 1702 is arranged in the vicinity of a corner of a frame line 103 of an enclosure plane of an X-ray image taking apparatus 1701. In this drawing, reference numeral 1703 denotes an object and a case where the right arm of a person is positioned along a diagonal line of the frame line 103 is illustrated as an example.

Figure 18:
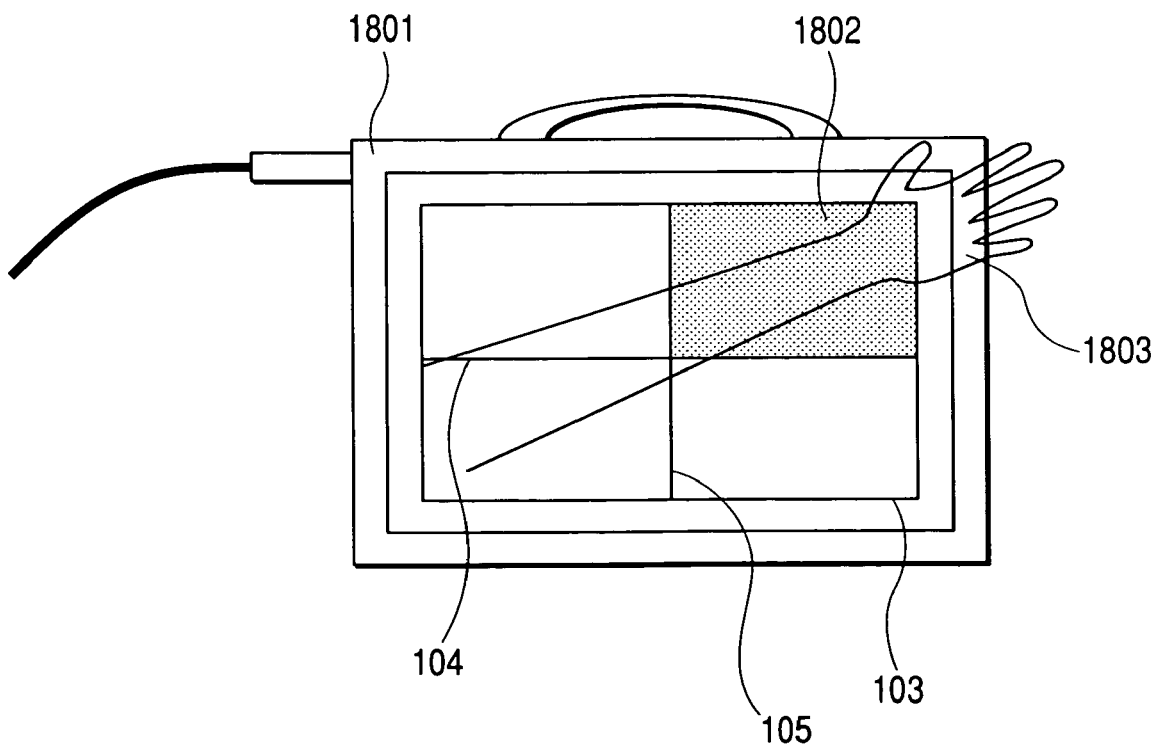
FIG. 18 is a plan view illustrating a schematic construction of an X-ray image taking apparatus of an eleventh embodiment.

FIG. 18 shows an eleventh embodiment where the color tint in a region 1802 divided by center lines 104 and 105 of an enclosure plane of an X-ray image taking apparatus 1801 is set so as to be different from those in other regions. That is, in this embodiment, the region 1802 is displayed so as to be distinguished from the other regions.

Figure 19:
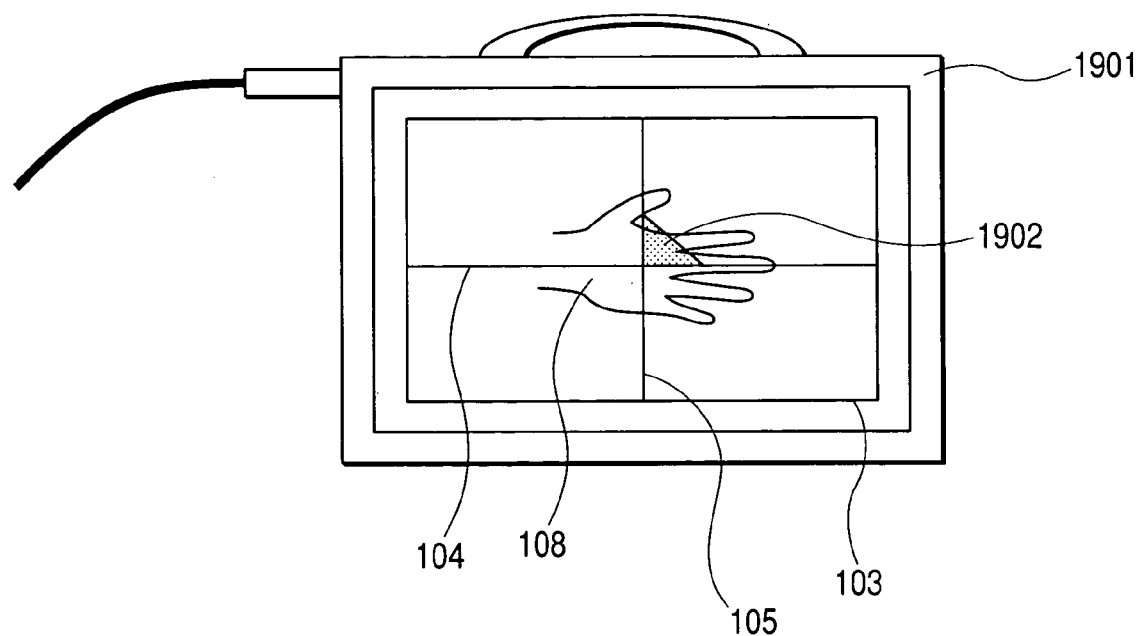
FIG. 19 is a plan view illustrating a schematic construction of an X-ray image taking apparatus of a twelfth embodiment.

FIG. 19 shows a twelfth embodiment where the color tint in a region 1902 in the vicinity of the intersection of center lines 104 and 105 of an enclosure plane of an X-ray image taking apparatus 1901 is set so as to be different from those in other regions, thereby setting the region 1902 as an indicator.

Figure 20:
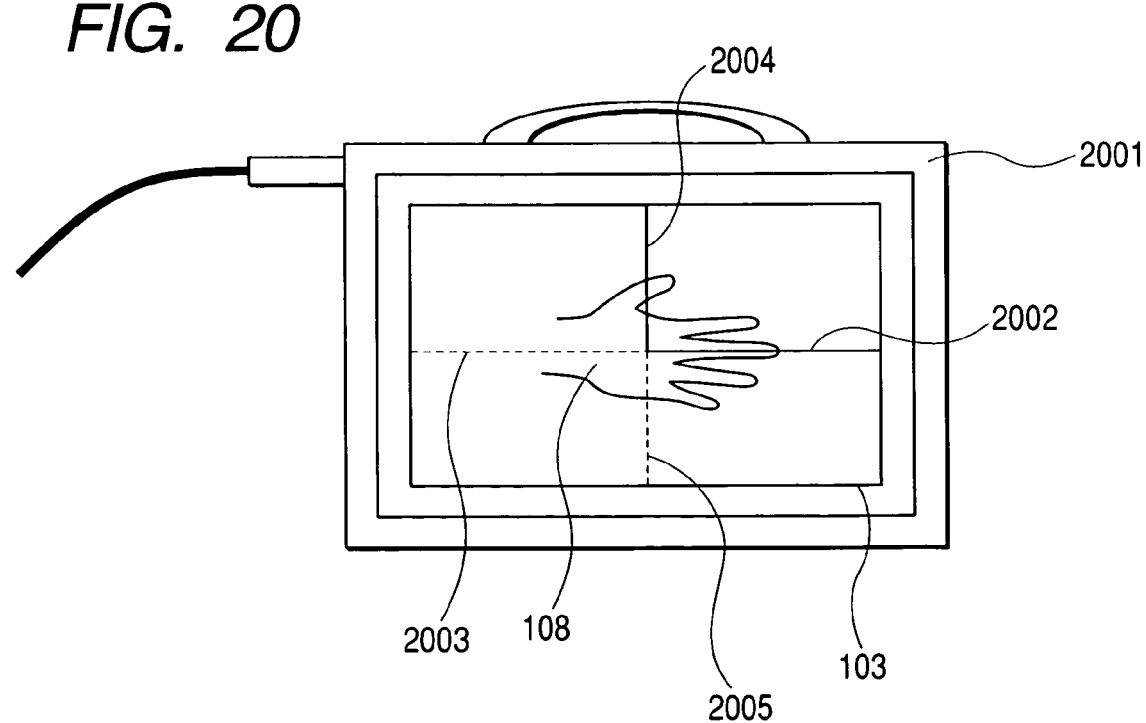
FIG. 20 is a plan view illustrating a schematic construction of an X-ray image taking apparatus of a thirteenth embodiment.

FIG. 20 shows a thirteenth embodiment where a center line extending between the long sides of an enclosure plane of an X-ray image taking apparatus 2001 and a center line extending between the short sides of the enclosure plane are divided at their centers and solid line portions 2002 and 2004 and dotted line portions 2003 and 2005 are displayed so as to be distinguished from each other.

Figure 21:
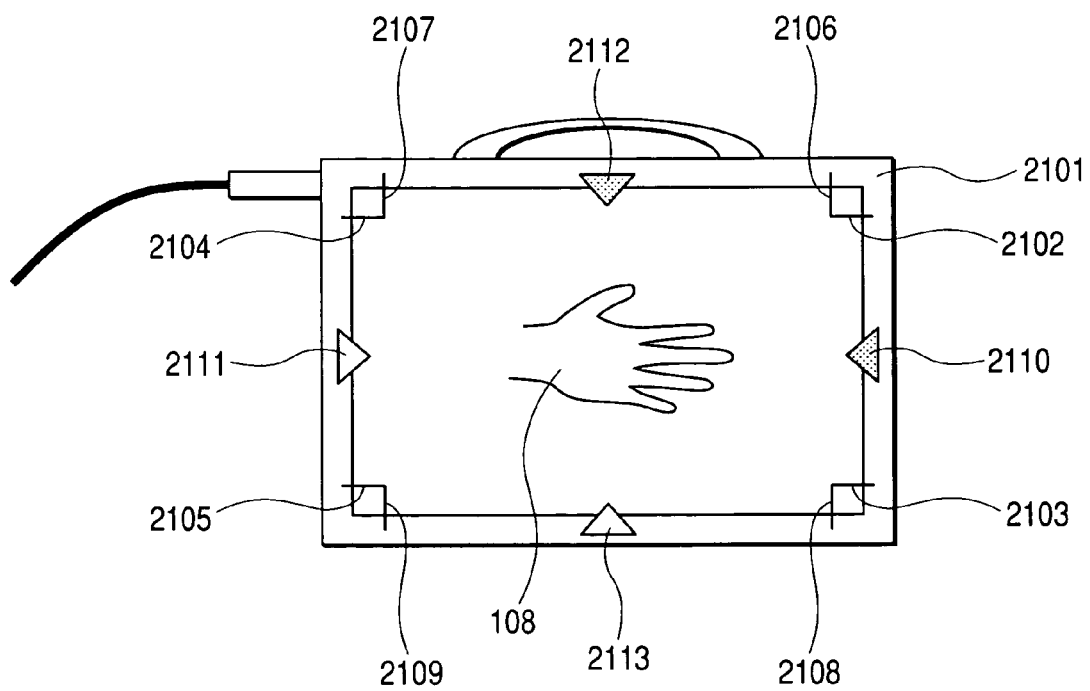
FIG. 21 is a plan view illustrating a schematic construction of an X-ray image taking apparatus of a fourteenth embodiment.
Figure 22:
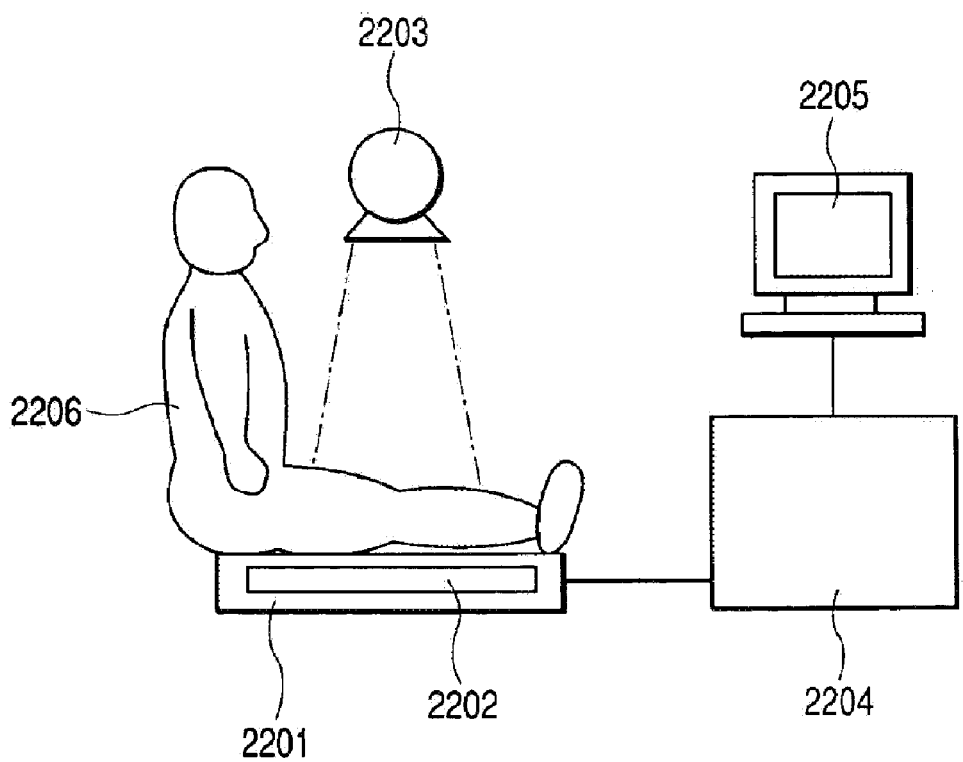
FIG. 22 is an explanatory diagram of a conventional radiation image taking system.
Figure 23:
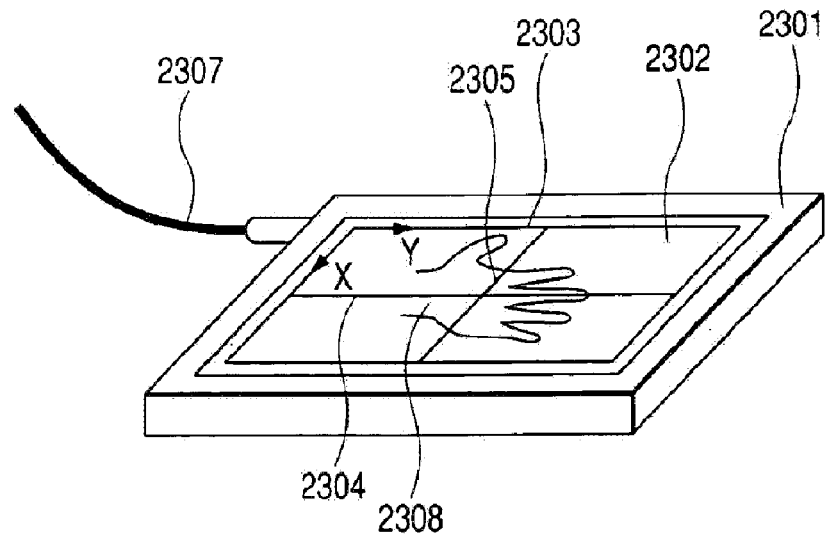
FIG. 23 is a perspective view illustrating a schematic construction of a conventional X-ray image taking apparatus.
Figure 24:
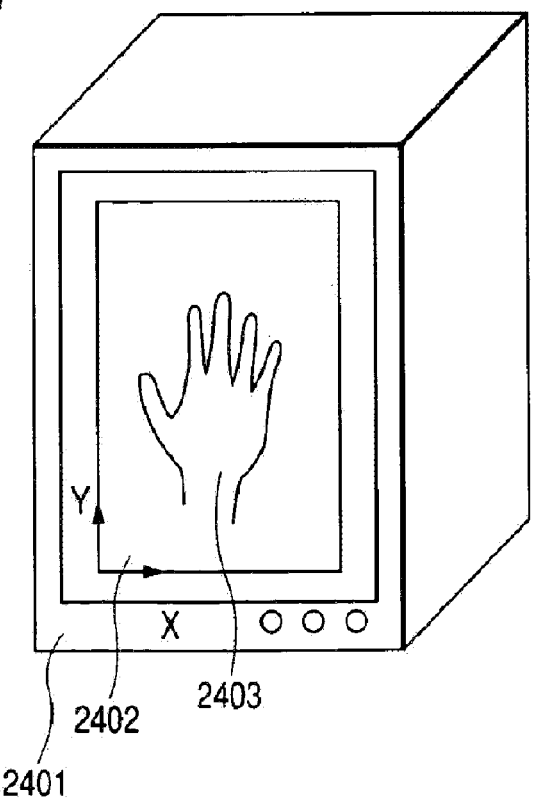
FIG. 24 is a perspective view illustrating an example of conventional displaying on a monitor.
Figure 25:
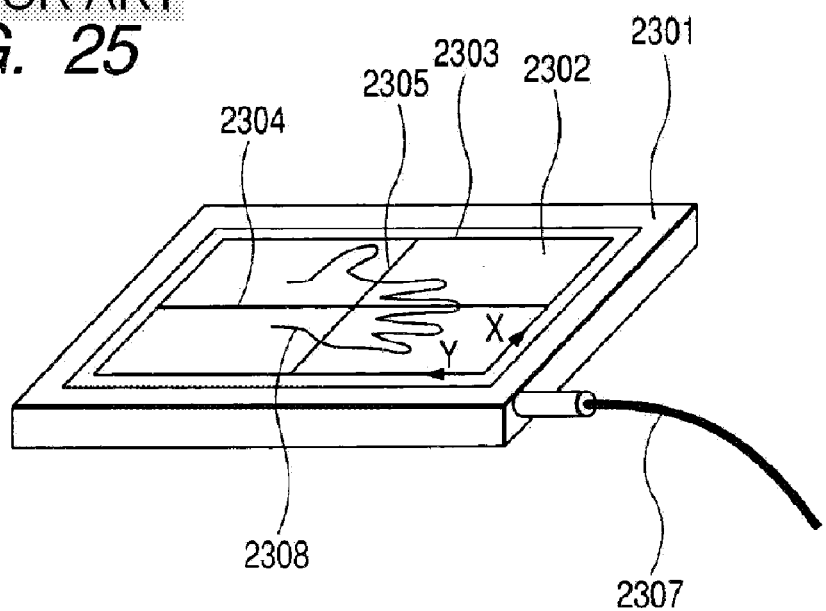
FIG. 25 is another perspective view illustrating the schematic construction of the conventional X-ray image taking apparatus.
Figure 26:
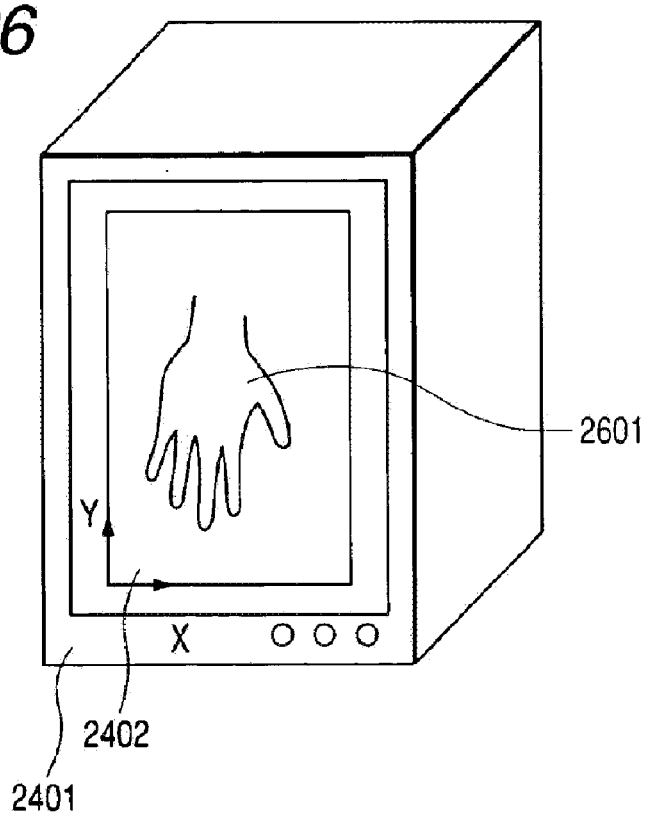
FIG. 26 is a perspective view illustrating another example of the conventional displaying on the monitor.

FIG. 21 shows a fourteenth embodiment where instead of the frame line 103, indicators 2102, 2103, 2104, and 2105 indicating a range in a short-side direction of a rectangular detection area and indicators 2106, 2107, 2108, and 2109 indicating a range in a long-side direction thereof are arranged for an enclosure plane of an X-ray image taking apparatus 2101. Also, indicators 2110 and 2111 indicating the center in the short-side direction and indicators 2112 and 2113 indicating the center in the long-side direction are provided. Further, the opposing indicators 2110 and 2111 are set so as to have different color tints and the opposing indicators 2112 and 2113 are set so as to have different color tints. In this manner, the indicators 2110 to 2113 are set as indicators of rotation within a detection plane.

The present invention is not limited to the embodiments described above and various modifications are conceivable.

For instance, in each embodiment described above, a case where the enclosure of the X-ray image-taking apparatus is provided with a communication cable and a grip has been described as an example, although it is not necessarily required to provide the communication cable and the grip for the enclosure. Also, the enclosure may have a shape that is rotation-symmetric within the detection plane. Further, the detection plane of the X-ray detection means is not limited to the rectangular shape.

As described above, with the X-ray image taking apparatus according to the present invention that is a transportable apparatus, flexibility in alignment at the time of image taking is increased by making it possible to maintain an appropriate relative positional relationship between the original point of an electronic image and an object at all times with reference to the indicators. Therefore, it becomes possible to display an image of the same part in the same desired direction at all times. As a result, it becomes possible to eliminate the necessity to perform image rotation work to an appropriate direction each time image confirmation is performed at the time of image taking or each time an image interpretation is made, which makes it possible to increase work efficiency.

When each indicator for discrimination of a rotation direction is arranged in the vicinity of its corresponding center line of a detection plane, it also becomes easy to arrange an object in the center portion of the detection plane.

When each indicator for discrimination of a rotation direction has a length that is approximately equal to the length of its corresponding side of the outer frame of a detection plane, there rarely occurs a situation where the indicator is hidden behind an object, which facilitates confirmation.

When each indicator for discrimination of a rotation direction exists in the vicinity of two sides of an outer frame or in the vicinity of one corner thereof, in particular when positioning is performed along a diagonal line of the rectangular shape of a detection plane, it becomes easy to recognize a specific corner of the detection plane.

It should be noted here that it is possible to realize the control means and the image processing means described in the first to fourteenth embodiments with a computer. Therefore, it is to be understood that an object of the present invention may also be accomplished by supplying a system or an apparatus with a storage medium storing a program code of software that realizes the functions of the above-mentioned embodiments and causing a computer (or a CPU or an MPU) of the system or the apparatus to read out and execute the program code stored in the storage medium.

In this case, the program code itself read out from the storage medium realizes the functions of the above-mentioned embodiments, which means that the storage medium storing the program code also constitutes the present invention.

Examples of the storage medium for supplying the program code include a flexible disk, a hard disk, an optical disk, a magneto-optical disk, a CD-ROM, a CD-R, a magnetic tape, a nonvolatile memory card, a ROM, and the like.

Also, it is needless to mention that, the functions of the above-mentioned embodiments may be accomplished not only by executing the program code read out by the computer but also by causing an operating system (OS) or the like running on the computer to perform a part or all of actual processing based on instructions of the program code.

Further, needless to say, the functions of the above-mentioned embodiments may be accomplished by writing the program code read out from the storage medium into a memory provided on a function expansion board inserted into the computer or a function expansion unit connected to the computer and then causing a CPU or the like provided on the function expansion board or the function expansion unit to perform a part or all of the actual processing based on instructions of the program code.

With the construction described above according to the present invention, the X-ray image taking apparatus according to the present invention provides an effect that it is possible for an image taking person to recognize the positional relationship between the X-ray image taking apparatus and an object with ease.

This application claims priority from Japanese Patent Application No. 2003-209517 filed on Aug. 29, 2003, which is hereby incorporated by reference herein.

What is claimed is:

1. A radiation image taking apparatus comprising:
   a radiation image acquisition portion that converts a radiation image transmitted through an object into an electronic image and outputs the electronic image;
   an image taking direction designation portion that designates an image taking direction of the object;
   a display portion that displays the image taking direction of the object on at least one plane of the radiation image acquisition portion;
   a coordinate conversion portion that performs coordinate conversion of the electronic image; and
   a control portion that controls the displaying of the image taking direction by the display portion and the coordinate conversion by the coordinate conversion portion based on the image taking direction designated by the image taking direction designation portion.

2. A radiation image taking apparatus according to claim 1, further comprising:
   a second display portion that displays a post-coordinate-conversion electronic image.

3. A radiation image taking apparatus according to claim 1, wherein the display portion is formed by one of
   an indicator that is capable of being electrically turned on/off, and
   an indicator that is capable of being selectively exhibited/hidden by means of a mechanical mechanism.

4. A radiation image taking apparatus according to claim 1, wherein the display portion is formed by a two-dimensional screen and displays a two-dimensional image.

5. A radiation image taking apparatus according to claim 1, wherein the display portion is arranged outside a detection area of the radiation image acquisition portion.

6. A radiation image taking apparatus according to claim 3, wherein the indicator is arranged in a vicinity of one of a center line in a long-side direction of a detection area of the radiation image acquisition portion constructed in a rectangular form and a center line in a short-side direction thereof.

7. A radiation image taking apparatus according to claim 1, wherein when a gravity center position of a detection plane of the radiation image acquisition portion is set as a rotation center, the display portion performs the displaying in a not-rotation-symmetric manner.

8. A radiation image taking apparatus according to claim 1, further comprising:
   a storage portion for storing information concerning a part name of the object and the image taking direction of the object to be associated with each other, wherein when the information concerning the part name of the object is inputted by the image taking direction designation portion, the control portion controls the displaying of the image taking direction by the display portion and the coordinate conversion by the coordinate conversion portion based on the image taking direction associated with the inputted information.

9. A radiation image taking method with which an image taking direction of an object is displayed on at least one plane of a radiation image acquisition portion, comprising:
   an image taking direction designation step for designating the image taking direction of the object;
   a radiation image acquisition step for converting a radiation image transmitted through the object into an electronic image and outputting the electronic image;
   a coordinate conversion step for performing coordinate conversion of the electronic image;
   a display step for displaying the image taking direction of the object on the at least one plane of the radiation image acquisition portion; and
   a control step for controlling the displaying of the image taking direction in the displaying step and the coordinate conversion in the coordinate conversion step based on the image taking direction designated in the image taking direction designation step.

10. A computer-readable medium comprising a control program for causing a computer to execute the radiation image taking method according to claim 9.

11. A radiation image taking system comprising:
a radiation generation apparatus that irradiates radiation; and
a plurality of devices connected in a mutually communicable manner, at least one of the plurality of devices comprising the radiation image taking apparatus according to claim 1.

12. A radiation image taking system comprising:
a radiation generation apparatus that irradiates radiation; and
a plurality of devices connected in a mutually communicable manner, at least one of the plurality of devices comprising the radiation image taking apparatus according to claim 2.

13. A radiation image taking system comprising:
a radiation generation apparatus that irradiates radiation; and
a plurality of devices connected in a mutually communicable manner, at least one of the plurality of devices comprising the radiation image taking apparatus according to claim 3.

14. A radiation image taking system comprising:
a radiation generation apparatus that irradiates radiation; and
a plurality of devices connected in a mutually communicable manner, at least one of the plurality of devices comprising the radiation image taking apparatus according to claim 4.

15. A radiation image taking system comprising:
a radiation generation apparatus that irradiates radiation; and
a plurality of devices connected in a mutually communicable manner, at least one of the plurality of devices comprising the radiation image taking apparatus according to claim 5.

16. A radiation image taking system comprising:
a radiation generation apparatus that irradiates radiation; and
a plurality of devices connected in a mutually communicable manner, at least one of the plurality of devices comprising the radiation image taking apparatus according to claim 6.

17. A radiation image taking system comprising:
a radiation generation apparatus that irradiates radiation; and
a plurality of devices connected in a mutually communicable manner, at least one of the plurality of devices comprising the radiation image taking apparatus according to claim 7.

18. A radiation image taking system comprising:
a radiation generation apparatus that irradiates radiation; and
a plurality of devices connected in a mutually communicable manner, at least one of the plurality of devices comprising the radiation image taking apparatus according to claim 8.

* * * * *

UNITED STATES PATENT AND TRADEMARK OFFICE
CERTIFICATE OF CORRECTION

PATENT NO. : 7,092,491 B2 Page 1 of 1
APPLICATION NO. : 10/927976
DATED : August 15, 2006
INVENTOR(S) : Keiji Okoda It is certified that error appears in the above-identified patent and that said Letters Patent is hereby corrected as shown below:

On The Coverpage
At item (73), please delete "Kaish" and insert --Kaisha--.

Signed and Sealed this

Twenty-first Day of November, 2006

JON W. DUDAS
*Director of the United States Patent and Trademark Office*